United States Patent
Little

(10) Patent No.: US 11,944,542 B2
(45) Date of Patent: *Apr. 2, 2024

(54) INFLATABLE PENILE PROSTHESIS CYLINDERS

(71) Applicant: Boston Scientific Scimed, Inc., Maple Grove, MN (US)

(72) Inventor: Eric F. Little, Shakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/303,816

(22) Filed: Jun. 8, 2021

(65) Prior Publication Data

US 2021/0290393 A1    Sep. 23, 2021

Related U.S. Application Data

(63) Continuation of application No. 16/052,388, filed on Aug. 1, 2018, now Pat. No. 11,051,943, which is a continuation of application No. 14/861,396, filed on Sep. 22, 2015, now Pat. No. 10,070,956.

(60) Provisional application No. 62/054,478, filed on Sep. 24, 2014.

(51) Int. Cl.
*A61F 2/26* (2006.01)

(52) U.S. Cl.
CPC ........ *A61F 2/26* (2013.01); *A61F 2250/0003* (2013.01)

(58) Field of Classification Search
CPC ........................... A61F 2/26; A61F 2250/0003

USPC ...................................................... 600/38–41
See application file for complete search history.

(56) References Cited

U.S. PATENT DOCUMENTS

| 4,726,360 A | 2/1988 | Trick et al. |
| 4,773,403 A | 9/1988 | Daly et al. |
| 5,067,485 A | 11/1991 | Cowen et al. |
| 5,069,201 A * | 12/1991 | Zinner ............. A61F 2/26 600/40 |
| 5,669,870 A | 9/1997 | Elist |

(Continued)

FOREIGN PATENT DOCUMENTS

| CN | 2063805 U | 10/1990 |
| CN | 2201072 Y | 6/1995 |

(Continued)

OTHER PUBLICATIONS

International Preliminary Report on Patentability for PCT Application PCT/US2015/051684, dated Apr. 6, 2017, 7 pages.

(Continued)

*Primary Examiner* — Samuel G Gilbert
(74) *Attorney, Agent, or Firm* — Brake Hughes Bellermann LLP

(57) ABSTRACT

An implantable inflatable penile prosthesis cylinder includes an outer tube member having a longitudinal axis, an inner tube member contained within the outer tube member, and one or more tensile support members within the inner tube member. The inner tube member includes at least one inflatable chamber section, at least a portion of which is defined by a wall of the inner tube member. The one or more tensile support members extend between interior surfaces of the wall and are placed in tension when the at least one chamber section is in an inflated state.

20 Claims, 2 Drawing Sheets

(56) References Cited

U.S. PATENT DOCUMENTS

| | | | |
|---|---|---|---|
| 10,070,956 B2* | 9/2018 | Little | A61F 2/26 |
| 11,051,943 B2* | 7/2021 | Little | A61F 2/26 |
| 2011/0087337 A1 | 4/2011 | Forsell et al. | |
| 2016/0081801 A1 | 3/2016 | Little | |

FOREIGN PATENT DOCUMENTS

| | | | | |
|---|---|---|---|---|
| CN | 2587355 Y | 11/2003 | | |
| CN | 1859882 A | 11/2006 | | |
| CN | 101160106 A | 4/2008 | | |
| EP | 3197398 A1 | 8/2017 | | |
| WO | 2010087769 A1 | 8/2010 | | |
| WO | 2013096615 A1 | 6/2013 | | |
| WO | WO-2013096615 A1 * | 6/2013 | | A61F 2/26 |
| WO | 2016049158 A1 | 3/2016 | | |

OTHER PUBLICATIONS

International Search Report and Written Opinion for PCT Patent Application No. PCT/US2015/051684, dated Nov. 27, 2015, 9 pages.

Extended European Search Report for European Application No. 20174838.1, dated Sep. 15, 2020, 6 pages.

First Office Action for Chinese Application No. 201580051209.3, dated Nov. 6, 2017, 8 pages.

* cited by examiner

INFLATABLE PENILE PROSTHESIS CYLINDERS

CROSS-REFERENCE TO RELATED APPLICATIONS

This application is a Continuation of, and claims priority to, U.S. patent application Ser. No. 16/052,388, filed on Aug. 1, 2018, entitled "INFLATABLE PENILE PROSTHESIS CYLINDERS", now U.S. Pat. No. 11,051,943, which is a continuation of U.S. patent application Ser. No. 14/861,396, filed on Sep. 22, 2015, entitled "INFLATABLE PENILE PROSTHESIS CYLINDERS", now U.S. Pat. No. 10,070,956, which claims priority to U.S. Patent Application No. 62/054,478, filed on Sep. 24, 2014, entitled "PENILE PROSTHESIS CYLINDERS", the disclosures of which are incorporated by reference herein in their entirety.

FIELD OF THE INVENTION

The invention generally relates to penile prostheses and, more specifically, to inflatable penile prosthesis cylinders.

BACKGROUND OF THE INVENTION

Erectile dysfunction (ED) or impotence is the inability to get or keep an erection that is firm enough, or lasts long enough, to have successful sexual intercourse. It can have serious effects on a person's sexual relationship and their self-esteem.

Inflatable penile prostheses may be used to cure or compensate for impotence. Inflatable penile prostheses typically include a pair of inflatable cylinders and a pump. The cylinders are implanted in the corpus cavernosa of the patient, and the pump is implanted in the scrotum of the patient. For some inflatable penile prostheses (i.e., three-piece penile prostheses), a separate fluid reservoir must be implanted in the abdomen of the patient. Alternatively, the fluid reservoir may be combined with the cylinders (i.e., two-piece penile prostheses).

Both the three-piece and the two-piece penile inflatable prostheses rely on the transfer of a volume of fluid to and from the inflatable cylinders to transition the cylinders between inflated and deflated states. It is desirable to reduce this volume of fluid to reduce the amount of pumping required to be performed by the patient, and to reduce the size of the prosthesis.

SUMMARY

Embodiments of the invention are directed to an implantable inflatable penile prosthesis cylinder and a penile prosthesis. In one embodiment, the implantable inflatable penile prosthesis cylinder includes an outer tube member having a longitudinal axis, an inner tube member contained within the outer tube member, and one or more tensile support members within the inner tube member. The inner tube member includes at least one inflatable chamber section, at least a portion of which is defined by a wall of the inner tube member. The one or more tensile support members extend between interior surf aces of the wall and are placed in tension when the at least one chamber section is in an inflated state.

One embodiment of the penile prosthesis includes a pair of inflatable penile prosthesis cylinders, a reservoir containing a fluid, and a pump. Each penile prosthesis cylinder includes an outer tube member having a longitudinal axis, an inner tube member contained within the outer tube member, and one or more tensile support members within the inner tube member. The inner tube member includes at least one inflatable chamber section, at least a portion of which is defined by a wall of the inner tube member. The one or more tensile support members extend between interior surfaces of the wall. The pump is configured to transfer fluid from the reservoir into the at least one inflatable chamber section to transition the at least one inflatable chamber section and the penile prosthesis cylinders to an inflated state. The one or more tensile support members are placed in tension when the at least one chamber section is in the inflated state.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
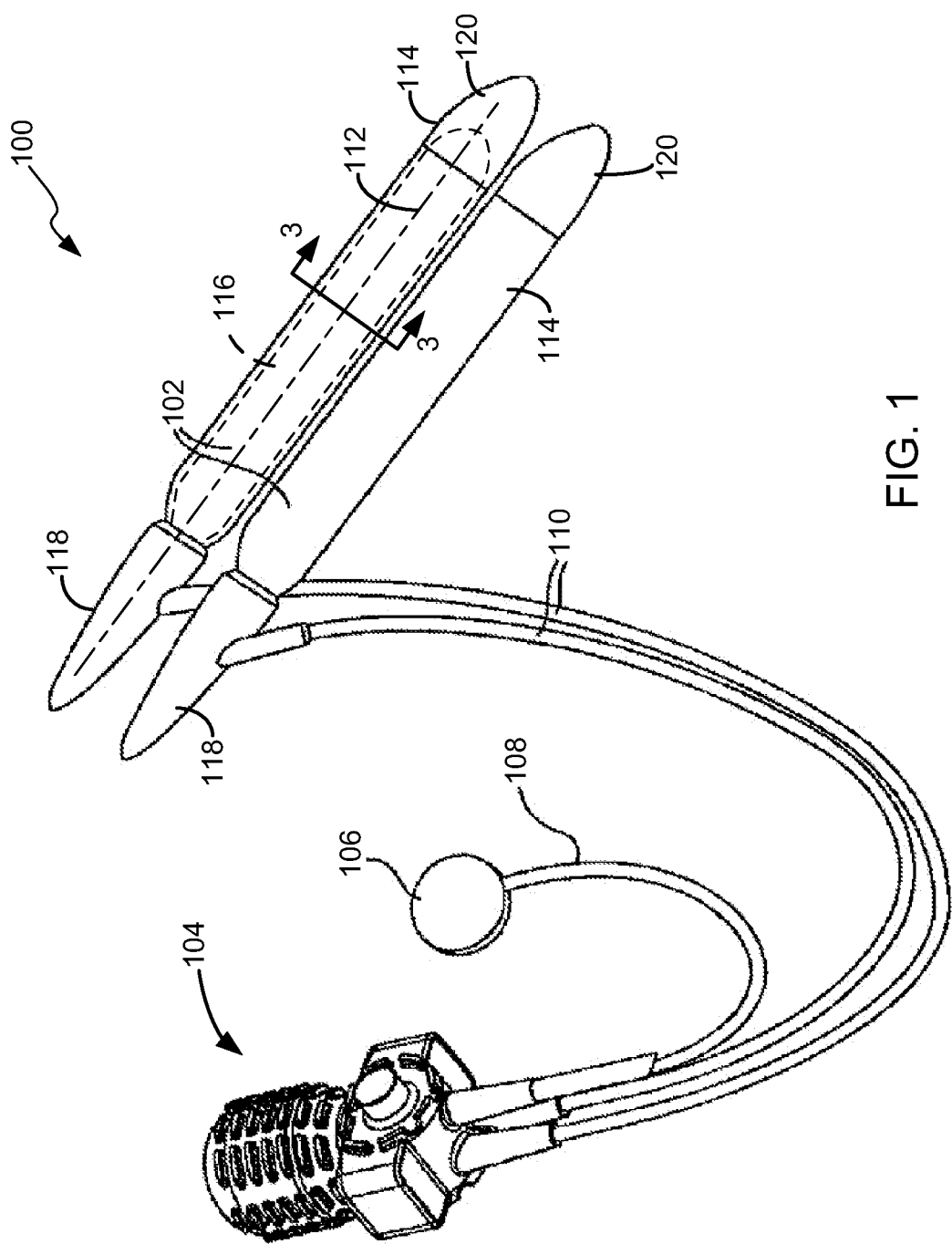
FIG. 1 is a schematic perspective view of an exemplary penile prosthesis comprising cylinders in accordance with one or more embodiments of the invention.

Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present, and both of these options are covered by the term. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic perspective view of an exemplary penile prosthesis 100 comprising inflatable cylinders 102 that are configured for implantation in the corpus cavernosa of a patient and are formed in accordance with one or more embodiments described herein. In some embodiments, the cylinders 102 have a unique inner tube geometry that allows for inflation of the cylinders 102 using less fluid than conventional penile prosthesis cylinders. While the exemplary penile prosthesis 100 is depicted as a three-piece inflatable penile prosthesis, the cylinders 102 may also be used with two-piece inflatable penile prostheses or other penile prostheses that utilize inflatable cylinders, as is readily apparent to those skilled in the relevant art.

In some embodiments, the penile prosthesis 100 includes a pump 104, a reservoir 106, tubing 108 fluidically coupling the reservoir 106 to the pump 104, and tubing 110 fluidically coupling the pump 104 to the cylinders 102. Fluid is pumped from the reservoir 106 through the tubing 108 and the tubing 110 to each of the cylinders 102 using the pump 104 to inflate the cylinders 102 to place them in an inflated or rigid state corresponding to an erect penis condition. The cylinders 102 may then be deflated using conventional techniques that transfer fluid from the cylinders 102 back to the reservoir 106 through the tubing 110 and 108.

In some embodiments, each penile prosthesis cylinder 102 has a longitudinal axis 112 oriented along the length of the cylinder 102, as shown in FIG. 1. In some embodiments, each cylinder 102 includes an outer tube member 114 and an inner tube member 116 contained within the outer tube member 114. The outer tube member 114 has a longitudinal axis that is approximately coaxial to the longitudinal axis 112 of the cylinder 102.

The cylinders 102 may also comprise conventional components, such as a rear tip 118, an end cap 120, and fluid conduit fluidically connecting the tubing 110 to one or more inflatable chambers contained within the outer tube member 114. The rear tip 118 and the end cap 120 can be used to seal the cylinder 102 and form a closed system, once implanted, in relation to the external environment of the corpus cavernosum. The cylinders 102 may also comprise conventional components that are not shown in the drawings in order to simplify the illustrations.

In some embodiments, the cylinders 102 are formed using conventional penile prosthesis cylinder materials that are medically safe and provide a necessary degree of structural reliability. For instance, the outer tube member 114 and the inner tube member 116 may be formed of silicone or polyurethane. Components of the cylinders 102 may also comprise synthetic materials such as various types of rubbers, neoprene, nylon, PVC, polystyrene, polyethylene, polypropylene, and bio compatible polymers known to those skilled in the art.

In some embodiments, the outer tube member 114 is the portion of the penile prosthesis cylinder 102 that is in direct contact with the lumen of the corpus cavernosum when implanted. However, it is understood that a sheath or other component may be inserted between the outer tube member 114 and the corpus cavernosum. In some embodiments, the outer tube member 114 provides an enclosure for the inner tube member 116, as well as conventional components, such as an internal reservoir, fluid flow paths or block, and other components.

In some embodiments, the inner tube member 116 comprises one or more inflatable chamber sections 122 that are fluidically coupled to a source of fluid, such as the reservoir 106. In some embodiments, the one or more chamber sections are inflated by receiving a volume of the fluid, such as through the actuation of the pump 104. In some embodiments, this inflation of the chamber sections 122 causes the girth or diameter of the outer tube member 114 to expand and/or stiffen, and places cylinder 102 in the inflated state.

In some embodiments, the chamber sections 122 of the inner tube member 116 allow for a reduced volume of fluid to be used to transition the cylinder 102 from a deflated state, corresponding to a flaccid penis condition, to the inflated state, corresponding to an erect penis condition, as compared to conventional penile prosthesis cylinders. As a result, the penile prosthesis 100 can operate utilizing a smaller volume fluid source, such as a smaller reservoir 106, than conventional penile prostheses. Additionally, transitioning the penile prosthesis from the deflated state to an inflated state may be accomplished by the patient with fewer actuations of the pump 104 due to the lower volume of fluid that must be transferred to the cylinders 102. As a result, transitioning of the cylinders 102 from the deflated state to the inflated state requires less effort than when conventional cylinders are used.

Figure 2:
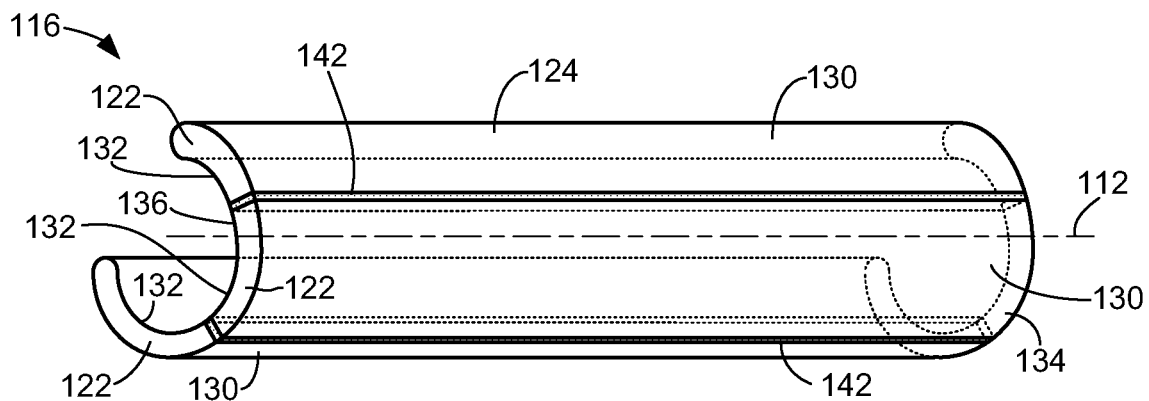
FIG. 2 is a simplified isometric view of an inner tube member in accordance with embodiments of the invention.
Figure 3A:
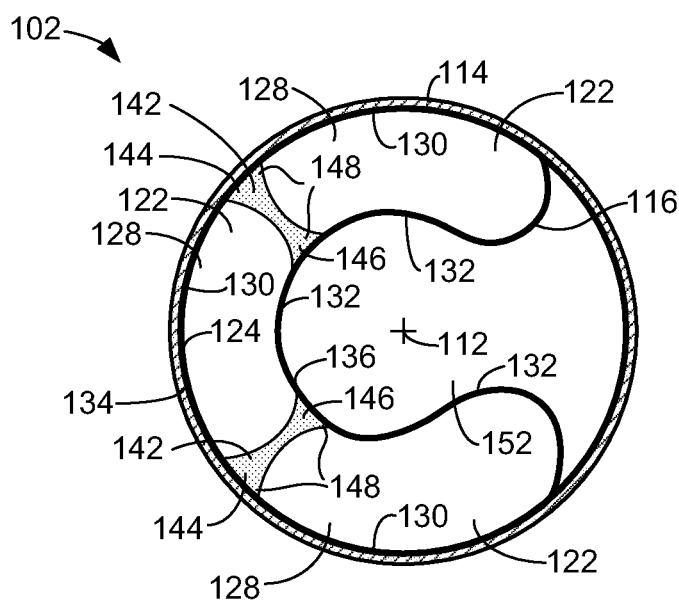
FIGS. 3A and 3B are cross-sectional views of an exemplary inflatable penile prosthesis cylinder taken generally along line 3-3 of FIG. 1 respectively in inflated and deflated states in accordance with embodiments of the invention.
Figure 3B:
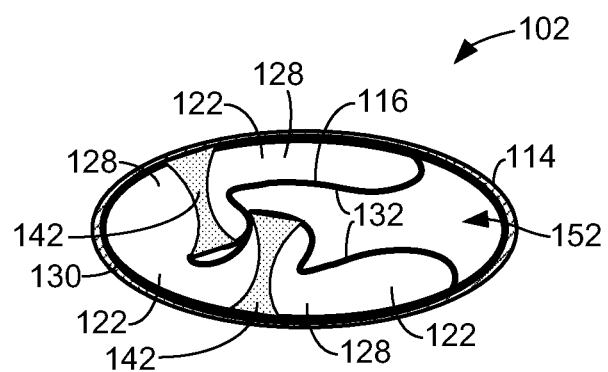

FIG. 2 is a simplified isometric view of an inner tube member 116 in accordance with embodiments of the invention. FIGS. 3A and 3B are simplified cross-sectional views of the exemplary cylinder 102 of FIG. 1 taken generally along line 3-3 in accordance with embodiments of the invention, and respectively in inflated in deflated states. Thus, the cross-sectional view of FIGS. 3A and 3B are of sections of the cylinder 102 in a plane extending perpendicularly to the longitudinal axis 112.

As mentioned above, the inner tube member 116 comprises one or more inflatable chamber sections 122 that are contained within the outer tube member 114. Each chamber section 122 is configured to inflate (i.e., expand like a balloon) from a deflated condition in response to the pumping of fluid from the reservoir 106 into the chamber sections 122 using the pump 104. In some embodiments, the inner tube member 116 includes at least three chamber sections 122. In some embodiments, the chamber sections 122 are each individually inflatable. In some embodiments, one or more of the chamber sections 122 are each divisions of a larger chamber and, therefore, inflate together.

In some embodiments, the inner tube member 116 is a separate structure in relation to the outer tube member 114. In some embodiments, walls of the inner tube member 116 completely define the chamber sections 122. In some embodiments, each of the chamber sections 122 includes a wall 124 that encloses at least a portion of an interior cavity 128 of the chamber section 122, in at least a plane extending perpendicular to the longitudinal axis 112, as shown in FIG. 3A. In some embodiments, the chambers 122 each share a portion of a single wall 124.

In some embodiments, the inflated cross-sectional shape of the inner tube member 116 is dissimilar to the cross-sectional shape of the outer tube member 114, as shown in FIG. 3A. That is, the shape of a portion of the exterior wall 124 of each chamber section 122 that is in a plane, which is perpendicular to the longitudinal axis 112, does not entirely conform to the outer tube member 114, as shown in FIG. 3A.

In some embodiments, inflation of the chamber sections 122 through the pumping of fluid into the interior cavities 128 using the pump 104, causes the chamber sections 122 to inflate to an inflated state, such as illustrated in FIG. 3A. In some embodiments, the inflation of the chamber sections 122 expand a girth or radial diameter of the outer tube member 114 in response to the outward radial pressure relative to the axis 112 generated by the chamber sections 122, to place the cylinder 102 in the inflated state.

In some embodiments, portions 130 of the wall 124 press toward the outer tube member 114 in a radial direction relative to the axis 112 when the chamber sections 122 are in their inflated state, as shown in FIG. 3A. In some embodiments, the portions 130 of the wall 124 face the outer tube member 114 and generally conform to the outer tube member 114, when the cylinder 102 or chamber 122 is in a fully inflated state. As used herein, the term "inflated state" means the inflated state of the chamber or chambers 122 that places the inflatable cylinder 102 in a rigid condition representing an erect penis condition. This is distinguishable from a deflated state of the cylinder 102 or chambers 122, shown in FIG. 3B, that represents a flaccid condition of the penis, or a state that represents a condition that is between the erect and flaccid conditions.

In some embodiments, the wall 124 of each chamber 122 includes a portion 132 that does not conform to the outer tube member 114 when the cylinder 102 is in the inflated state, as shown in FIG. 3A. In some embodiments, the portions 130 and 132 are generally located on opposing sides of the cavity 128, as shown in FIGS. 2 and 3A. In some embodiments, the portions 132 are displaced from the outer tube member 114 a greater distance than the portions 130. In some embodiments, the portions 132 do not directly press outwardly against the outer tube member 114 in a radial direction relative to the axis 112 when the cylinder 102 or chamber sections 122 are in the inflated state. That is, the portions 132 are not directly constrained by the outer tube member 114 when the chamber sections 122 and the cylinder 102 are in the inflated state, as shown in FIG. 3A. In some embodiments, each portion 132 faces the central or longitudinal axis 112 of the outer tube member 114 or the cylinder 102, as shown in FIG. 3A.

In some embodiments, the portion or portions 130 of the wall 124 form a convex section 134 when the chamber sections 122 are in the inflated state, as shown in FIG. 3A. In some embodiments, the portion or portions 132 of the wall 124 form a concave section 136 when the chamber sections 122 are in the inflated state, as shown in FIG. 3A.

In some embodiments, the inner tube member 116, or portions thereof, such as portions 130, are allowed to slide relative to the outer tube member 114. A coating, such as Parylene™ may be applied to the inner surface of the outer tube member 114 and/or to the outer surface of the wall 124 of the inner tube member, to provide a slippery, wear-resistant interface between the inner tube member 116 and the outer tube member 114.

In some embodiments, the contact between the chamber sections 122 of the inner tube member 116 and the outer tube member 114 may be mechanical, chemical or both. Thus, the inner tube member 116, when inflated, may be disposed upon the inner surface of the outer tube member 114 to cause the outer tube member 114 to become rigid when the chamber sections 122 are inflated. The inner tube member 116 may also be chemically coupled to the inner surface of the outer tube member 114 at various contact points, which remain attached to the outer tube member 114 during inflated and deflated states of the cylinder 102.

In some embodiments, the chamber sections 122 of the inner tube member 116 may be defined by the portions 130 and the outer tube member 114. That is, the portions 130 of the wall 124 are replaced by the adjoining wall of the outer tube member 114. The portions 132 of the wall 124 form a seal against the outer tube member 114 to at least partially form or define the inflatable chambers 122.

In some embodiments, each cylinder 102 includes one or more tensile support members 142 within the inner tube member 116, as shown in FIGS. 2, 3A and 3B. In some embodiments, each tensile support member 142 extends between interior surfaces of the wall 124. In some embodiments, the tensile support members 116 extend between opposing interior surfaces of the wall 124, as shown in FIG. 3A, or the tensile support members 142 extend between the wall 124 and the outer tube member 114. In some embodiments, when the chambers 122 or the cylinder 102 are inflated, the tensile support members 142 are placed in tension, as they limit the separation of the opposing sides of the wall 124. In some embodiments, the tensile support members 142 operate to constrain the shape of the inner tube member 116 to facilitate radial expansion of the outer tube member 114 when the one or more chamber sections 122 are inflated.

In some embodiments, the tensile support members 142 extend along the longitudinal axis 112 of the cylinder along at least a portion of the length of the inner tube member 116, as shown in FIG. 2. In some embodiments, the tensile support members 142 define side walls of the chamber sections 122, and may separate adjoining chamber sections 122, as shown in FIG. 3A.

In some embodiments, the tensile support members 142 are formed through an extrusion process, a molding process, or other suitable process. In some embodiments, the tensile support members 142 are formed with the formation of the inner tube member 116. In some embodiments, the tensile support members 142 are formed separately from the tube member 116 and opposing ends 144 and 146 of each support member 142 are attached to the portions 130 and 132, or the portion 132 and the outer tube member 114, using an adhesive or other suitable fastening technique. In some embodiments, each of the tensile support members 142 includes one or more fillets 148 at the ends 144 and 146, as shown in FIG. 3A.

As mentioned above, in some embodiments, the tensile support members 142 are placed in tension when the one or more chambers 122 of the tube member 116 are inflated. In some embodiments, the tensile support members 142 assist in preventing the portion 126 of the wall 124 from expanding or herniating into the central space 152 around the axis 112 when the one or more chambers 122 of the inner tube member 116 are inflated. The thickness of each of the tensile support members 142 is selected to be sufficient to prevent the expansion of the portions 132 into the central space 152.

Embodiments of the cylinders 102 described above allow for the central space 152 to form in response to the inflation of the one or more chamber sections 122 with fluid. Unlike conventional inflatable penile prosthesis cylinders, the central space 152 defines a volume within the outer tube member 114 that does not need to be filled with fluid in order to transition the cylinder 102 from the deflated or flaccid condition to an inflated or erect condition. Rather, the cylinder 102 only requires fluid to be driven into the chamber sections 122 to transition the cylinder 102 to the inflated or erect condition. As a result, inflatable penile prosthesis cylinders 102 can be transitioned between their inflated and deflated conditions through the transfer of less fluid than is required for conventional penile prosthesis cylinders. This allows the reservoir 106 to be formed smaller than conventional penile prosthesis reservoirs due to the low volume of fluid required to operate the penile prosthesis 100.

As the chamber sections 122 are deflated through the removal of fluid from the interior cavities 128 using conventional techniques, the cylinder 102 transitions to the deflated state, as illustrated in FIG. 3B. This deflation of the chamber sections 122 causes a reduction in the pressure exerted by the chamber sections 122 on the inner surface of the outer tube member 114, allowing the outer tube member 114 to contract radially relative to the longitudinal axis 112. In some embodiments, the radial contraction of the cylinder 102 also results in a reduction in the rigidity of the cylinder 102.

The foregoing examples have focused on elongated, continuous tensile support members 142 which extend along the longitudinal axis 112 of the cylinder 102, thereby dividing the inner tube member 116 into a plurality of longitudinally-extending chamber sections 122. It should be appreciated, however, that other arrangements of the support members 142 and/or the chamber sections 122 are within the scope of the present invention insofar as they constrain the inner tube member 116 such that, when the inner tube member 116 is inflated, it extends along at least a portion of the circumference of the cylinder 102 and forms a central space 152 that occupies volume within the outer tube member 114. For instance, in some embodiments (not pictured), a plurality of discontinuous tensile support members 142 are arranged so as to extend along all or part of the longitudinal axis 112 of the cylinder 102, and/or to extend along all or part of a circumference of the inner tube member 116. The tensile support members 142 in these embodiments are optionally spaced in a regular pattern and/or spaced a fixed-distance from one another.

In other embodiments, the tensile support members 142 comprise one or more fenestrations, such that fluid can pass between the longitudinally-extending chamber sections. In some embodiments, the inner tube member 116, when inflated, extends about the entire circumference of the outer tube member 114, while in other embodiments, it extends about 90%, 80%, 70%, 60%, 50%, 40%, (or any value therebetween) of the circumference of the outer tube member 114.

More generally, some embodiments of the present invention include an inflatable inner tube member 116 nested within an outer tube member 114, in which the inflatable inner tube member 116 inflates such that it occupies a portion of the volume of the cylinder 102 and defines, either by itself or in cooperation with the outer tube member 114, a void or space within the outer tube member, thereby permitting the cylinder 102 to be inflated without filling its entire volume with an inflation fluid.

Some embodiments are directed to a method of operating the penile prosthesis 100 formed in accordance with one or more of the embodiments described above. In one embodiment, the pump 104 is actuated to draw a quantity of fluid from the reservoir 106 and drive the fluid into each of the chamber sections 122. The chamber sections 122 expand and become rigid in response to the reception of the fluid. In some embodiments, this inflation of the chamber sections 122 produces a radial force against the outer tube member 114, which radially expands the outer tube member 114 and/or stiffens the outer tube member 114 to place the cylinder 102 in the inflated state. In some embodiments, the cylinder 102 is returned to the deflated state by venting the inflatable chambers 122 of the fill fluid by allowing the fill fluid to return to the reservoir 106.

Although the present invention has been described with reference to preferred embodiments, workers skilled in the art will recognize that changes may be made in form and detail without departing from the spirit and scope of the invention.

What is claimed is:

1. An implantable inflatable penile prosthesis cylinder comprising:
    an outer tube member having a longitudinal axis;
    an inner tube member contained within the outer tube member, the inner tube member comprising at least one inflatable chamber section, wherein at least a portion of each chamber section is defined by a wall of the inner tube member; and
    one or more tensile support members within the inner tube member, each tensile support member extending between interior surfaces of the wall;
    wherein the one or more tensile support members include a first end portion, a second end portion, and a middle portion, the middle portion having a width that is smaller than a width of the first end portion, the middle portion having a width that his smaller than a width of the second end portion,
    wherein the one or more tensile support members are in tension when the at least one chamber section is in an inflated state.

2. The penile prosthesis cylinder according to claim 1, wherein a section of the wall that is in a plane extending perpendicular to the longitudinal axis includes a first portion that presses toward the outer tube member in a radial direction relative to the longitudinal axis, when the at least one chamber section is in the inflated state.

3. The penile prosthesis cylinder according to claim 2, wherein the section of the wall includes a second portion that is displaced from the outer tube member a greater distance than the first portion, when the at least one chamber section is in the inflated state.

4. The penile prosthesis cylinder according to claim 2, wherein the section of the wall includes a second portion that faces the longitudinal axis, when the at least one chamber section is in the inflated state.

5. The penile prosthesis cylinder according to claim 2, wherein the section of the wall includes a second portion that is not directly constrained by the outer tube member, when the at least one chamber section is in the inflated state.

6. The penile prosthesis cylinder according to claim 2, wherein the first portion includes a convex section, and the second portion includes a concave portion, when the at least one chamber section is in the inflated state.

7. The penile prosthesis cylinder according to claim 1, wherein the one or more tensile support members each extend along the longitudinal axis.

8. The penile prosthesis cylinder according to claim 7, wherein the first end portion and the second end portion of the one or more tensile support members are attached to opposing interior sides of the wall.

9. The penile prosthesis cylinder according to claim 8, wherein the first end portion and the second end portion the one or more tensile support members include fillets.

10. The penile prosthesis cylinder according to claim 1, wherein the at least one chamber section comprises a plurality of chamber sections, and the one or more tensile support members separate adjoining chamber sections.

11. The penile prosthesis cylinder according to claim 1, wherein the at least one chamber section comprises a plurality of chamber sections, and the one or more tensile support members each define a side wall of one of the inflatable chamber sections.

12. A penile prosthesis comprising:
a pair of inflatable penile prosthesis cylinders, each penile prosthesis cylinder comprising:
an outer tube member having a longitudinal axis;
an inner tube member contained within the outer tube member, the inner tube member comprising at least one inflatable chamber section, wherein at least a portion of each chamber section is defined by a wall of the inner tube member; and
one or more tensile support members within the inner tube member, each tensile support member extending between interior surfaces of the wall, the one or more tensile support members include a first end portion, a second end portion, and a middle portion, the middle portion having a width that is smaller than a width of the first end portion, the middle portion having a width that his smaller than a width of the second end portion;
a reservoir containing fluid; and
a pump configured to transfer fluid from the reservoir into the at least one inflatable chamber section to transition the at least one chamber section and the penile prosthesis cylinders to an inflated state;
wherein the one or more tensile support members are in tension when the at least one chamber section is in the inflated state.

13. The penile prosthesis according to claim 12, wherein the one or more tensile support members each extend along the longitudinal axis and the first end portion and the second end portion of the one or more tensile support members are attached to opposing interior sides of the wall.

14. The penile prosthesis according to claim 13, wherein the at least one chamber section comprises a plurality of chamber sections, and the one or more tensile support members separate adjoining chamber sections.

15. The penile prosthesis according to claim 12, wherein a section of the wall that is in a plane extending perpendicular to the longitudinal axis includes a first portion that presses toward the outer tube member in a radial direction relative to the longitudinal axis, and a second portion that is not directly constrained by the outer tube member, when the at least one chamber section is in the inflated state.

16. An implantable inflatable penile prosthesis cylinder comprising:
an inner tube member extending along a longitudinal axis; and
a plurality of tensile support members within the inner tube member, each tensile support member extending between interior surfaces of a wall of the inner tube member, the one or more tensile support members include a first end portion, a second end portion, and a middle portion, the middle portion having a width that is smaller than a width of the first end portion, the middle portion having a width that his smaller than a width of the second end portion;
wherein the tensile support members are tensioned when the inner tube member is in an inflated state.

17. The penile prosthesis cylinder according to claim 16, further comprising an outer tube member, wherein the inner tube member is within an interior cavity of the outer tube member and encompasses a subset of a volume of the interior cavity when in the inflated state.

18. The penile prosthesis cylinder according to claim 17, wherein the inner tube member extends about less than 90% of the circumference of the outer tube member.

19. The penile prosthesis cylinder according to claim 17, wherein the inner tube member includes a plurality of inflatable chamber sections within the inner tube member that extend along the longitudinal axis.

20. The penile prosthesis cylinder according to claim 19, wherein the tensile support members separate adjoining chamber sections.

* * * * *